Figure 1:
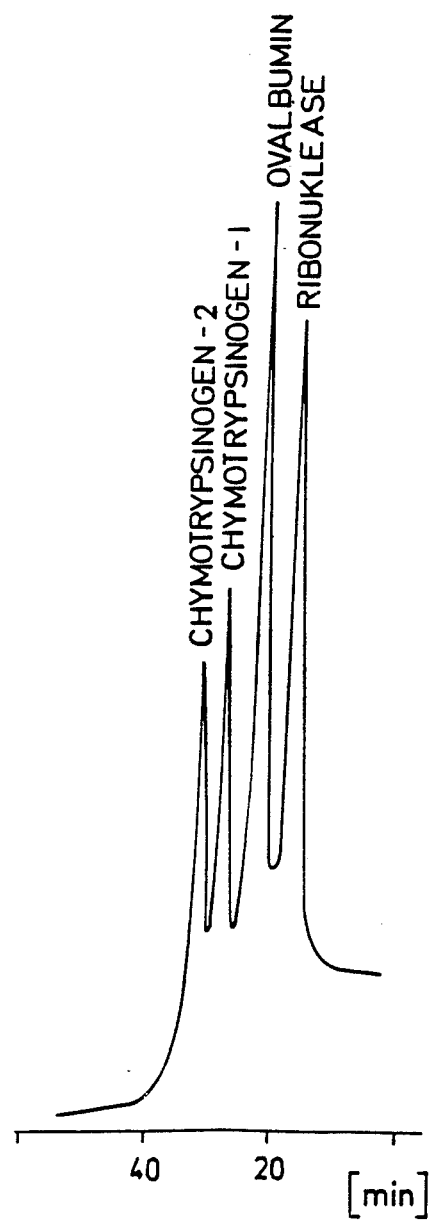

United States Patent [19]

Svec et al.

[11] Patent Number: 4,923,610
[45] Date of Patent: May 8, 1990

[54] MACROPOROUS POLYMERIC MEMBRANES FOR THE SEPARATION OF POLYMERS AND A METHOD OF THEIR APPLICATION

[75] Inventors: Frantisek Svec, Hrebec, Czechoslovakia; Boris G. Belenkii, Leningrad, U.S.S.R.

[73] Assignee: Ceskoslovenska akademive ved and Akademia Nauk SSSR, Praha, Czechoslovakia

[21] Appl. No.: 411,665

[22] Filed: Sep. 25, 1989

Related U.S. Application Data

[62] Division of Ser. No. 281,266, Dec. 7, 1988, Pat. No. 4,889,632.

[30] Foreign Application Priority Data

Dec. 10, 1987 [CS] Czechoslovakia ............... 9034-87
Oct. 21, 1988 [CS] Czechoslovakia ............... 6987-88

[51] Int. Cl.$^5$ .............................................. B01D 13/00
[52] U.S. Cl. ................................ 210/637; 210/639; 210/654
[58] Field of Search ............... 210/634, 637, 639, 644, 210/649-654

[56] References Cited

U.S. PATENT DOCUMENTS 4,634,531  1/1987  Nakagawa et al. ............... 210/639
4,659,474  4/1987  Perry et al. ............... 210/639

Primary Examiner—Frank Sever
Attorney, Agent, or Firm—Leydig, Voit & Mayer

[57] ABSTRACT

An object of the invention are macroporous polymeric membranes, suitable above all for the separation of polymers, which consists of the copolymer of a monovinyl monomer, selected from the group comprising acrylates, methacrylates, vinylpyridine, N-vinylpyrrolidone, vinyl acetate, and hydroxystyrene, with a divinyl monomer, selected from the group comprising alkylene and hydroxyalkylene diacrylates and dimethacrylates, divinylbenzene, and divinylpyridine, at the ratio of monomers of both types ranging from 5:95 to 95:5 wt. %. The membranes are formed from polymeric globular entities which have the size 0.05 to 0.5 μm and are interconnected by covalent bonds, whereas communicating voids—pores occur between the globuli.

The total thickness of membranes is 0.2 to 15 mm. and their specific surface area, which is measurable also in the dry state, may attain 400 m$^2$/g. Glycidyl methacrylate is advantageously used as the monovinyl monomer in the amount 5-80 vol. % related to the total volume of monomers. Ethylene dimethacrylate is advantageously used in the amount 20-95 vol. % related to the volume of monomers as the divinyl monomer. The membranes contain on their inner surface covalently bound allyl, hydroxyl, amine, sulfonate, hydrogensulfonate, thiol, and/or alkyl groups containing up to 18 carbon atoms and may be reinforced in their whole cross-section with an insert.

Another object of the invention is the method for preparation of macroporous polymeric membranes consisting in placing a mixture of monomers and a radical initiator, dissolved in a porogenic inert organic solvent selected from the group comprising alcohols, esters of carboxylic acids, ketones, and their mixtures, into a space of an adapted shape formed by two temperature-controlled plates and a distance insert having the thickness corresponding to the required thickness of membrane and heating up to 80° C. for 24 hours at utmost in order to carry out the radical polymerization. Azo-bis-isobutyronitrile is advantageously used as an initiator in the amount 0.05-2 wt. % related to monomers in the polymerization mixture. Cyclohexanol or its mixture containing up to 20 vol. % dodecanol are advantageously used as a porogenic solvent in the amount 40-60 vol. % in the polymerization batch. Further object of the invention is the method of application of macroporous membranes, where a sector made from the membrane is placed on a base fixing its position and enabling the outlet of liquid passing through the membrane, which base create a wall of a chamber. The chamber is filled with a solution of polymer or polymer mixture, the solution passes through the membrane under pressure up to 1 MPa, the polymer or polymers are sorbed in the membrane, and then a solvent with properties changing according to the purposeful program is introduced into the chamber and individual components of the separated mixture are eluted and detected and/or collected. The properties of solvent changing according to the program may be pH, ionic strength, temperature, or concentration of an organic solvent miscible with water.

1 Claim, 3 Drawing Sheets

MACROPOROUS POLYMERIC MEMBRANES FOR THE SEPARATION OF POLYMERS AND A METHOD OF THEIR APPLICATION

This is a division of application Ser. No. 281,266 filed Dec. 7, 1988 now U.S. Pat. No. 4,889,632.

The invention pertains to macroporous polymeric membranes for the separation of polymers and to a method of their application. Although the problems of separation of macromolecules from their mixtures with both low-molecular weight and high-molecular weight compounds are very often concerned in the present literature and practice and considerable success was attained, they cannot be solved. The problem of an efficient separation of a product from reaction medium becomes the decisive criterion of the successful solution in modern fast developing scientific and technical disciplines, e.g., in biotechnology. As a rule, it is not a large problem to find a method for analytical identification of the searched compound or to determine its concentration. However, difficulty is caused by the still incompletely solved problem of preparative industrial separation with a high efficiency at reasonable extent of expended labour, energy, capital and material resources and at minimum or environmental loading.

The separation and isolation of biopolymers is most important from the aspcts of their application. This group of macromolecular compounds comprises oligopeptides and polypeptides, proteins, enzymes, lectins, antibodys, antigens, nucleic acids, and polysaccharides. The separation of biopolymers from natural sources has been the generally known problem already since last century.

The original purification methods consisted above all in precipitation, e.g., of proteins, or in their salting out with neutral salts, which may be carried out also at the parallel variation of pH and thus obtain even multiple fractionation in one step. But also then, a long way led to obtaining a pure protein, which was crowned with success first in 1926, when Sumner isolated crystalline urease. Nevertheless, the effect of ionic strength or pH is used again in the separation of proteins, as will be shown later.

A method, named by its inventor M. Cvett chromatography (Ber. Deut. Botan. Ges., 24, 316, 1906), developed parallelly. However, first the work of A. J. P. Martin and R. L. M. Synge (Biochem. J., 35, 1358, 1941), who introduced the concept of theoretical plate into liquid chromatography, became an important landmark. It was also stated there that columns packed with microparticles are especially suitable for the separation of macromolecules, the diffusion coefficients of which are very low. Since microparticles were not yet discovered in that time, the process of high-performance liquid chromatography (HPLC) was realized first twenty years later.

The chromatography of polymers developed first on the basis of findings of Peterson and Sober (J. Amer. Chem. Soc., 76, 1711, 1954) that proteins may be adsorbed on the diethylaminoethyl derivative of cellulose and then gradually eluted by the solution with an increasing ionic strength. Also other cellulose derivatives were later used for the same purpose, e.g., carboxymethyl cellulose. At the end of fifties, the Pharmacia company in Uppsala, Sweden, introduced crosslinked dextran gels for size-exclusion chromatography (SEC) of proteins and nucleic acids (Ger. Patent 1,292,883; Brit. Patent 974,054), in which process the separation occurs on the basis of accessiability of various portions of the gel structure for species with a different size of macromolecule. But a low mechanical strength of gel media did not enable the full realization of HPLC principle.

A breakthrough occurred in the fractionation of bacitracin on microparticles of silica derivatized with alkylsilanes (K. Tsuji, J. H. Robinson; J. Chromatog., 112, 663, 1976). Several structure forms of this peptide were separated by the method of so-called reversed-phase liquid chromatography (RPLC) in a column 30 cm long using an acid mobile phase containing organic solvent. Soon after that, papers also appeared describing the application of silica for the high-performance size-exclusion chromatography (SEC) and ion-exchange liquid chromatography (IELC) of proteins with an almost quantitative yield and retained activity. In comparison to gel materials, almost by two orders of magnitude higher flow rates of mobile phase can be used in these cases and thus substantially reduce time of analysis.

Generally, macromolecules interact with the stationary phase in chromatographic column in various ways. This has a consequence that the capacity factor defined for an isocratic elution, i.e. the elution using the same solvent all the time, as $$K' = (t_R - t_o)/t_o$$

where $t_R$ is retention time of the searched compound and $t_o$ is the column dead time, dramatically changes at a slight change in the eluent composition. At certain composition, is so high that the macromolecule practically does not move in the column. However, a small change in the solvent causes a decrease in to a value close to zero and the macromolecule passes through the column without any interaction with the packing. The usually plotted and published dependence of log on the composition is thus very steep, often almost vertical. Consequently, the length of chromatographic column has not a decisive influence on the quality of separation. Very short columns may be used containing only such amount of sorbent which is necessary for the sorption of separated molecules in the amount required for the detection of compounds after separation.

It revealed, that in the chromatography of macromolecules, e.g., by the RPLC method, the resolution function is proportional to $$D_m^{\frac{1}{2}} d_p^{-1} t_G^{\frac{1}{2}},$$

where $D_m$ is diffusion coefficient of solute, $d_p$ is diameter of particles packed into the column, and $t_G$ is the time for which the composition of solvent mixture varies (gradient). Because the first quantity is a characteristic constant of the separated compound, the quality of separation may be improved by a small change in the composition of solvent or by decreasing the size of particles of column packing. In the first case, the time necessary for the separation of mixture increases, whereas in the secons case the pressure loss in the column increases and eluent has to be introduced under a very high pressure, which may reach several units or tens of MPa.

The given facts show that enlargement of the scale of chromatographic separation from an analytical or laboratory scale may be a considerable problem. It is obvious that application of large-volume columns with a relatively large diameter may cause difficulties, even if incompressible packings are used, which are manifested in results incomparable with those obtained in a small scale. So called tailing of chromatographic peaks or their overlapping often occur. The reason may be the different flow rate of eluent in various sites of the cross-section of column. Inorder to avoid this effect, a uniform rate of the horizontal front has to be attained thrugh the column in the direction from the inlet of eluent to the column outlet. This problem was discussed in the U.S. Pat. No. 3,250,058 and solved by breakers fitted inside the column. The method for influencing the flow of liquid in a column is concerned also in other patents (U.S. Pat. No. 3,539,505; Jap. Patent 73-68,752) and enables to increase the scale of separation, but to the detriment of the original simplicity. In order to overcome the complex design of column, some authors used an intervention into the packing as such (U.S. Pat. No. 3,856,681) or special methods for column packing (U.S. Pat. No. 4,211,656). It revealed later that a suitable effect can be obtained if small particles of the sorbent used for separation are incorporated into a porous inert matrix having a fibrous form. This fibrous material is then packed into the column of a special design, which than exhibits a far lower pressure loss and zone spreading (U.S. Pat. No. 4,384,957; U.S. Pat. No. 4,512,897; U.S. Pat. No. 4,496,461; U.S. Pat. No. 4,604,198).

As it was indicated above, most of packings of chromatographic columns for the separation of biopolymers are porous, concerning both the inorganic polymers (silica gel, glass) or organic polymers (styrene-divinylbenzene, acrylate or methacrylate copolymers, etc.), usually in the form of spherical particles (F. E. Renier, Chromatographia, 24, 241, 1987). These particles are produced predominantly by a suspension technique and, recently, also by the multistep dispersion method (seeded polymerization). On completion of the polymerization, except few cases, a narrow-size fraction of the sorbent has to be obtained from the raw product, since the quality of packed column and, consequently, also its efficiency strongly depends on the particle size distribution. The fractionation of particles is very tedious and the fraction of particles applicable for HPLC is only a small part of the entire raw product.

In view of the application of small-diameter particles (5–10 $\mu$m), also the organic sorbents have to be sufficiently mechanically resistant, which requires a relatively high concentration of a crosslinking agent in polymerization feed. The demand on porosity is solved at the same time by the synthesis of macroporous particles, i.e. particles which exhibit the porosity also in the dry state or thermodynamically poor solvents (Czech. Patent 168,268; Brit. Patent 1,512,462; Canadian Patent 1,049,194). From the aspects of morphology, the macroporous polymers are characterized by globular structure, i.e. the particles consist of mutually connected submicroscopic spherical entities called globules. Specific surface area of the macroporous polymers is then, as a matter of fact, the surface area of these globules and interstitial spaces between them are pores (see, e.g., Z. Pelzbauer et al., J. Chromatog., 171, 101, 1979). The globular structure of porous particle suggests to some extent a spherical body filled with small also spherical globules. Such suggestion is not far from the conditions occurring inside a packed chromatographic column, which however has the shape of a cylinder. Provided the column is packed with particles having the size of globules (0.1–0.4 $\mu$m), the chance for realization of the chromatographic separation will be negligible, because the pressure which should be developed is unrealistically high.

Membranes for electrodialysis, which have only the surface layer formed from a macroporous polymer, are concerned in U.S. Pat. No. 3,926,864. Such a surface has, after modification with ionogenic groups, significant antifouling properties. Because also suitable electrodialytic properties need to be achieved, the polymerization is carried out in such a way that the inner part of membranes is microporous (formed by gel). For this reason, these membranes cannot be used for the separation of polymers. They are suitable for desalination of water, removal of ions, and the like.

They are also known plates for thin-layer chromatography, where, however, the sorbent is deposited on a solid nonporous substrate (glass, metal). The layer is employed in the separation process, which comprises the features of chromatographic separation, in the tangential direction, i.e. in the path the length of which many times exceeds the particle size of sorbent. A disadvantage of thin layers, which are loose poured or bonded, is also a low resistance towards mechanical damage. The thin-layer chromatography can be utilized for preparative purposes only with difficulties.

The above given survey on the state of art clearly shows that not yet exists a reliable and simple method for the separation of polymers in larger scale. Therefore it was necessary to find a principally new solution, which is the object of the present invention.

The invention pertains to macroporous polymeric membranes, suitable above all for the separation of polymers, which consist according to the invention of the copolymer of a monovinyl monomer selected from the group comprising acrylates, methacrylates, vinylpyridine, N-vinylpyrrolidine, vinyl acetate, hydroxystyrene, with a divinyl monomer selected from the group comprising alkylene and hydroxyalkylene diacrylates and dimethacrylates, divinylbenzene, and divinylpyridine, whereas the mutual ratio of the both types of monomers ranges from 5:95 to 95:5 wt.%, and are formed from polymeric globular configurations with the size of 0.05 to 0.5 $\mu$m mutually connected by covalent bonds, while between the globular configurations are mutually communicating voids—pores. The total thickness of membrane is 0.2 to 15 mm and specific surface area, measurable also in the dry state, may attain the value as high as 400 m$^2$/g. The membranes may contain a reinforcing insert in their whole section in order to increase their mechanical strength.

Glycidyl methacrylate is advantageously used as the monovinyl monomer in the amount of 5–80 vol.% of the whole volume of monomers in the batch, while the residual part 20–95 vol.% is formed by the divinyl monomer, advantageously ethylene dimethacrylate. It is obvious at the same time, that an arbitrary mixture of both types of monomers may be used and, in this way, the porous properties of the formed membrane are varied. Also the selection of monomers may be broader. The monovinyl part may be also glycidyl acrylate, glycidyl itaconate, glycidyl vinyl ether, glycidyl vinyl adipate, and, if the reactivity of epoxide group can be given up, also many other monomers. Neither the selection of the crosslinking agent is final and many other agents may be chosen from the group comprising diacrylates and dimethacrylates having both vinyl groups connected by ester bonds with a chain of various length or of various hydrophilicity, or by divinylbenzene and others.

The membranes according to the invention are advantageously produced by placing the mixture of monomers, which are dissolved together with a radical initiator in a porogenic inert organic solvent selected from the group comprising alcohols, esters of carboxylic acids, ketones, and their mixtures, in a space adapted in the shape and formed by two temperature-controlled face plates and a distance insert having the thickness corresponding to the required thickness of membrane. Polymerization of the mixture is carried out by its heating to temperature up to 80° C. for 24 hours at utmost in the space of mold, while globules are formed during polymerization at the suitable combination of monomer, crosslinking agent, and inert solvent, which increase their size with the increasing conversion as far as they come into contact and their bonding occurs, thus providing the membrane with the desirable mechanical strength.

Azo-bis-isobutyronitrile is used in the amount of 0.05–2 wt.% related to the total amount of monomers in order to initiate the radical polymerization, but an arbitrary radical initiator may be used, which is selected from the group comprising azo compounds, peroxides, hydroperoxides, redox systems, and the like.

An important component of the polymerizing system is the porogenic solvent, the proportion of which in the polymerization batch amounts to 40–60 vol.%. Cyclohexanol or its mixture which as much as 20 vol.% of dodecanol can be advantageously used. Naturally, also other porogenic agents may be used which are selected from the group comprising aliphatic and aromatic alcohols, esters, ethers, ketones, hydrocarbons, silicon oil, low-molecular weight polymers, and others.

The polymeric porous membranes prepared according to the invention from reactive monomers can be further modified and thus broadly extent the choice of their properties. In this way, hydrophilicity or lyophilicity may be increased, ionogenic groups may be introduced, and catalysts, affinants, or other active groups or molecules can be immobilized.

For example, allyl, amine, sulfonate, hydrogensulfonate, hydroxyl, thiol, and alkyl groups with chain length up to 18 carbon atoms are covalently bound to the inner surface of membrane by chemical modification.

A fundamental object of this invention is also a method of application of the above described macroporous membranes. It consists in placing a sector of an arbitrary size and shape, which was obtained from the macroporous polymeric membrane, on a base securing a constant position on any of walls forming a part of chamber and enabling to collect liquid passing through the membrane. The chamber is filled with a solution of polymer or polymer mixture, which is allowed to pass through the membrane at the pressure lower than 1 MPa, while the polymer (polymers) is sorbed in the membrane. The solvent in which the polymer (polymers) was dissolved is introduced into the chamber by a pump and then properties of the solvent are changed according to the specific program in such a way, that individual components of the sorbed polymer are gradually again dissolved and eluted from the membrane thus being separated. The course or separation is either only detected with a suitable equipment and the composition of the polymer or polymer mixture is qualitatively or quantitatively evaluated, or individual fractions are collected giving the components of separated mixture as individuals and the product (preparative separation).

The programmed change of properties of the solvent which causes the gradual dissolution of individual components of the mixture (gradient) may concern pH, ionic strength, content of organic solvent, temperature, and other variables.

The macroporous polymeric membranes for separation of polymers, particularly of biopolymers, and the method of this separation have numerous advantages in comparison with the present state of art. Above all, their preparation is very simple and is not limited with respect to their dimensions. The membranes are marked by their sufficient mechanical stability and resistance towards physical and chemical effects. The mechanical strength may be further increased, if it is desirable, by polymerization incorporation of a reinforcing insert into the membrane during its preparation. Because the membranes contain reactive groups, they may be readily chemically modified and functional groups changing their properties may be introduced onto their inner surface, thus susbstantially increasing their application possibilities. For example, separation of biopolymers proceeds, in comparison to earlier methods, very fast at a considerably higher loading of a weight unit of the separating element than is the possible loading of chromatographic columns. At the same time, the pressure which needs to be developed in order to obtain the required flow rate is by one to two orders of magnitude lower than in column methods of the comparable efficiency. A principal advantage of the membranes and the method of their application according to the invention is, however, the possibility to create theoretically unlimitedly large areas on which the separation of polymers occurs and thus to realize even an industrial process for obtaining individual compounds. The required area is not necessarily obtained by increasing the dimension of one membrane and one chamber, but it is possible to combine the needed number of smaller membranes and chambers into blocks fulfilling the same purpose.

The invention is further elucidated in the examples of real performance without limiting its scope to any of them.

EXAMPLE 1

A mold formed from two metallic plates with drilled communicated channels and a 1.2 mm thick distance insert of a square shape, made from silicon rubber, in which a square window with side length of 8 cm and a hole enabling to charge the mold space from outside are cut out, was charged with a polymerization mixture consisting of 0.6 g N-vinylpyrrolidone, 11.4 g ethylene diacrylate, 8.2 g 2-butanone, and 0.15 g azo-bis-isobutyronitrile (polymerization initiator). Water 80° C. warm was led into the mold for 8 hours. On completion of the polymerization, the mold was disassembled and the prepared membrane having the specific surface area 8.4 $m^2/g$ was ready to use. The size of individual globules determined by electron microscopy was 0.48 μm.

EXAMPLE 2

The same mold as in example 1 was charged with a mixture consisting of 0.6 g glycidyl methacrylate, 11.4 g ethylene dimethacrylate, 0.12 g initiator, and 16.2 g cyclohexanol and the polymerization was carried out under the same conditions. The prepared membrane had the specific surface area 139 m²/g; globular configurations had the diameter 0.05 μm.

EXAMPLE 3

A mold, the distance insert of which was 15 mm thick, was charged with a mixture consisting of 12 ml 2-hydroxyethyl acrylate, 12 ml 2-hydroxypropylene diacrylate, 0.24 g azo-bis-isobutyronitrile, 32.4 ml cyclohexanol, and 3.6 ml dodecanol. The polymerization was carried out for 3 hours at 60° C. and then for 5 hours at 80° C. The prepared polymeric board had the specific surface area 38 m²/g; monodisperse globules had the diameter 0.12 μm.

EXAMPLE 4

A mold, the distance insert of which had thickness 3 mm and was provided with a cut circular window with radius 4 cm, was charged with a mixture consisting of 4.8 g of 4-hydroxystyrene, 6.2 g of 2,3-dihydroxybutylene dimethacrylate, 0.15 g azo-bis-isobutyronitrile, and 12.8 g methyl benzoate. The polymerization was carried out at 80° C. for 24 hours and the final product in the form of a target with diameter 8 cm had the specific surface area 12.2 m²/g. Globules had the size 0.32 μm.

EXAMPLE 5

The same mold as in example 4 was charged with a solution of 7.2 ml glycidyl methacrylate, 4.8 ml ethylene dimethacrylate, and 0.12 g azo-bis-isobutyronitrile in a mixture of 16.2 ml cyclohexanol and 1.8 ml dodecanol. After 8 hours of polymerization carried out at 70° C., a membrane was obtained with the specific surface area 43.3 m²/g, which consisted of globules with the size 0.16 μm.

EXAMPLE 6

A gauze from polyester fiber with mesh size about 300 μm was inserted into a mold demarcated with a distance insert 3 mm thick. The mold, which cavity has a square section with side length 6C cm, was charged with a mixture containing 19% 2-vinylpyridine, 19% 2,4-divinylpyridine, 2% azo-bis-isobutyronitrile, and 60% cyclohexanol. The polymerization was completed at 80° C. after 18 hours and the resulting product had the specific surface area 18.9 m²/g.

EXAMPLE 7

The membrane obtained according to example 2 was immersed into a solution of potassium hydroxide in water with concentration 1 mol/l and allowed there at 60° C. for 18 hours. After washing the membrane with 0.5 mol/l solution of hydrochloric acid and water, it contained 1.4 mmol/g carboxylic groups.

EXAMPLE 8

The membrane obtained according to example 5 was heated for 3 hours in a 0.5 mol/l solution of sulfuric acid. The hydrolytic reaction led to the complete cleavage of epoxy groups to vicinal hydroxyl groups and thus to an increased hydrophilicity of membrane.

EXAMPLE 9

The membrane obtained according to example 5 was stirred with a 50% aqueous solution of trimethylammonium chloride for 10 hours at heating to 80° C. After washing with 0.5 mol/l aqueous solution of sodium hydroxide and water, 1.93 mmol/l of quaternary ammonium groups was determined in the product by titration. The product contained 2.7% nitrogen according to elemental analysis.

EXAMPLE 10

The membrane obtained according to example 8 was stirred with a 20% solution of chloride of hexadecanoic acid in benzene. After 6 hours of heating to 60° C., washing with benzene, methanol, and ether, and drying, the weight of product increased by 4.2% if compared with the initial weight, which corresponded to the 32% conversion of epoxide groups originally present.

EXAMPLE 11

A mold formed from two metallic plates with drilled communication channels and a 1 mm thick distance insert of square shape made from silicon rubber, in which a square window with side length 8 cm and a hole enabling to fill the mold from outside are cut out, was charged with a polymerization mixture consisting of 6 ml glycidyl methacrylate, 6 ml ethylene dimethacrylate, 0.12 g azo-bis-siobutyronitrile, 16.2 ml cyclohexanol, and 1.8 ml dodecanol. Water 70° C. warm was introduced into the mold channels for 8 hours. After the polymerization was completed, the mold was allowed to cool down and disassembled. A plate of macroporous membrane was thoroughly washed with alcohol, water and again with alcohol and allowed to dry. A circular target with diameter 10 mm was cut from the square plate with a stamp (surface area approx. 300 mm²). The specific surface area of membrane in the dry state was 62 m²/g.

EXAMPLE 12-18

The mold described in example 11 was charged with mixtures which composition is given in Table 1, the charge was polymerized and worked in the same way as in example 11.

TABLE 1

Composition of the polymerization mixture used in the preparation of macroporous polymeric membranes and their specific surface area

| Example | GMA ml | EDMA ml | AIBN g | CyOH ml | DoCH ml | $S_g$ m²/g |
|---|---|---|---|---|---|---|
| 12 | 4.8 | 7.2 | 0.12 | 18 | 0 | 80 |
| 13 | 7.2 | 4.8 | 0.12 | 16.2 | 1.8 | 45 |
| 14 | 9.6 | 2.4 | 0.12 | 17.1 | 0.9 | 160 |
| 15 | 0.6 | 11.4 | 0.12 | 18 | 0 | 260 |
| 16 | 7.2 | 4.8 | 0.12 | 18 | 0 | 53 |
| 17 | 0.6 | 11.4 | 0.06 | 18 | 0 | 250 |
| 18 | 7.2 | 4.8 | 0.24 | 14.4 | 3.6 | 35 |

GMA — glycidyl methacrylate. EDMA — ethylene dimethacrylate. AIBN — azo-bis-isobutyronitrile. CyOH — cyclohexanol. DoOH — dodecanol, and $S_g$ — specific surface area in the dry state determined by the dynamic method of the thermal desorption of nitrogen.

EXAMPLE 19

Circular targets from the macroporous membrane prepared according to example 13 were allowed in a 0.01 mol/l solution of NaOH in butanol for 24 hours. After the reaction was completed, the targets were washed with ethanol and water and stored for further application in the wet state.

EXAMPLES 20 AND 21

Epoxide groups of the membrane were modified with octanol or octadecanol in the same way as in the preceding example 19. In the later case, the modification was carried out at temperature 65° C.

EXAMPLE 22

Circular targets with diameter 10 mm stamped from the membrane defined in example 16 were immersed for 6 hours into a 25% commercial aqueous solution of ammonia and heated under reflux condenser to 80° C. The targets were then washed with water until the reaction on ammonia ceased. The elemental analysis proved the presence of 1.8 mmol/g amino groups in the modified polymer.

EXAMPLES 23-30

Targets from the membrane prepared according to example 11 were modified by the same procedure as in example 22 consisting in the reaction with the neat amine or its aqueous solution carried out in a flask or sealed ampoule. The reaction conditions and content of groups bound to the polymeric membrane are surveyed in Table 2.

TABLE 2

Reacton conditions for the modification of macroporous membrane and the content of groups bound to the product

| Example | Amine | Concentration of aq. solution wt. % | Reaction time h | Temp. °C. | Content of groups mmol/g |
|---|---|---|---|---|---|
| 23 | dimethyl- | 100 | 3 | 60 | 2.0 |
| 24 | 2-hydroxyethyl- | 100 | 6 | 70 | 2.2 |
| 25 | bis-2-hydroxyethyl- | 100 | 6 | 70 | 2.1 |
| 26 | octyl- | 100 | 12 | 70 | 0.4 |
| 27 | ethyl- | 50 | 6 | 80 | 1.6 |
| 28 | ethylenedi- | 50 | 10 | 80 | 1.7 |
| 29 | trimethyl- .HCl | 50 | 24 | 80 | 2.2 |
| 30 | tributyl- | 100 | 24 | 80 | 0.1 |

EXAMPLE 31

Circular targets stamped from the macroporous membrane prepared according to example 12 were immersed for 6 hours into 0.01 mol/l sulfuric acid and heated to 80° C. The targets were washed with water until the acid reaction ceased, dipped into a solution of 10.2 g NaOH in 36 ml water, and the mixture was cooled down to 0° C. Under stirring of the liquid above membranes, 24 g propansultone was dropwise added. After 30 minutes, the mixture was again heated to 35° C. and the reaction continued for further 3 hours. On completion of heating, the mixture was allowed at ambient temperature for 12 hours. The targets were washed with water, 0.5 mol/l HCl, and again with water until the acid reaction ceased. In this way 0.85 mmol/g sulfo groups was obtained on the surface of polymeric membrane.

EXAMPLE 32

A rectangle 10×5 cm obtained from the plate prepared in the similar way as in example 12, epoxide groups of which were hydrolyzed to vicinal dihydroxy derivative with diluted sulfuric acid in the same way as in example 31, was washed with water and dried. The dry plate was immersed for 5 hours into a mixture allyl glycidyl ether-dioxan (1:1 vol/vol) containing 0.3 vol.% boron fluoride etherate and heated to 50° C. The grafted allyl groups were then modified with a 30% potassium thiosulfate in water at ambient temperature for 24 hours, while oxygen from a cylinder was passed through the mixture every other 10 minutes for 10 minutes. After washing with water, 0.4 mol/l HCl, and again with water, the membrane contained 0.37 mmol/g sulfonate groups as it was determined by acidobasic titration.

EXAMPLE 33

A circular target with diameter 20 cm cut from a square plate with side length 25 cm and thickness 3 mm immersed into a glass dish containing 100 ml 1,2-dichloroethane and allowed there for 20 hours. Then, 45 ml sulfur trioxide monohydrate was slowly added at laboratory temperature under stirring by tilting the dish. The membrane was removed after one hour of reaction and washed with ethanol and water. Acidobasic titration of a sample revealed that the membrane contained 1.39 mmol/g hydrogensulfate groups.

EXAMPLE 34

Circular targets with diameter 30 mm, which were stamped from the plate prepared according to example 14, were mixed with a 10% aqueous solution of sodium sulfide. The mixture was moderately shaken at 25° C. for 12 hours. The targets were washed with water until the odour of hydrogen sulfide vanished. The modified polymer contained 0.52 mmol/g thiol groups.

EXAMPLE 35

A target with diameter approx. 1 cm from a 1-mm thick membrane prepared according to example 11 and modified according to example 19 was placed on a bottom of vessel with a circular cross-section and volume about 1 ml in such a way that, after filling the vessel with liquid, the whole flow occurred exclusively through the membrane. The content of vessel was agitated with a propeler stirrer. Eluent was introduced into the vessel by a pump according to a preselected gradient. Under the membrane, resting on a surface provided with a system of collection channels which secured a perfect and uniform outlet of eluent from every site of the membrane, also a central outlet capillary opening was provided, from which the passing eluent (or its part) was led into a detector and then may be collectedin order to obtain the separated compounds. The vessel was charged with a solution containing 0.1 mg ribonuclease, 0.1 mg ovalbumin, and 0.1 mg chymotrypsinogen in 0.02 mol/l phosphate buffer with pH 6.8 in which ammonium sulfate was dissolved to the concentration of 2 mol/l. The same buffer containing the decreasing amount of ammonium chloride was introduced into the vessel under stirring and pressure 0.1 MPa by the flow rate 0.5 ml/min. The state when the eluent contained 1% of the original amount of ammonium sulfate was reached after 35 minutes. The eluent flowing from the vessel was led into a UV detector Gilson. The record of detector response (chromatogram) is shown in FIG. 1. All originally absorbed proteins were eluted from the membrane in the yield of 100%.

EXAMPLE 36

Figure 2:
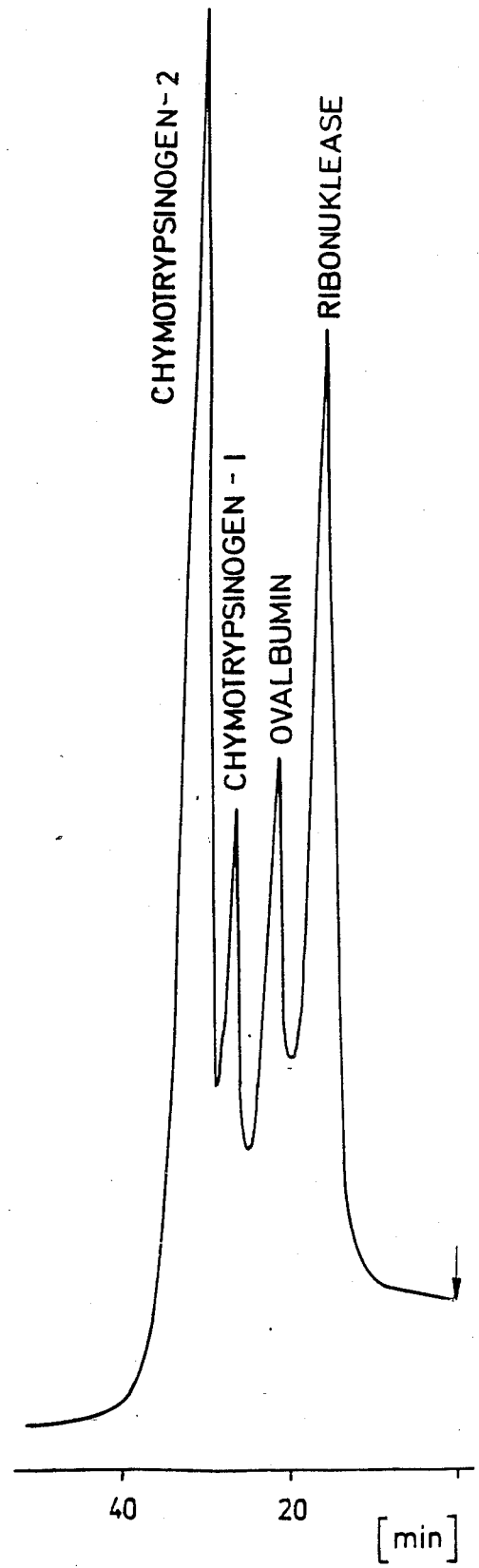

The same mixture of proteins as in example 35 was separated by the identical procedure and in the same equipment, but the target modified according to example 26 was employed. The chromatogram is shown in FIG. 2.

EXAMPLE 37

The same proteins as in example 35 were separated in the same equipment and under the identical conditions, but the amount of each protein in the solution charged into the vessel was 5 mg, i.e. 50 times higher. Absolutely the same separation as is shown in FIG. 1 was obtained.

EXAMPLE 38

Figures 3, 4:
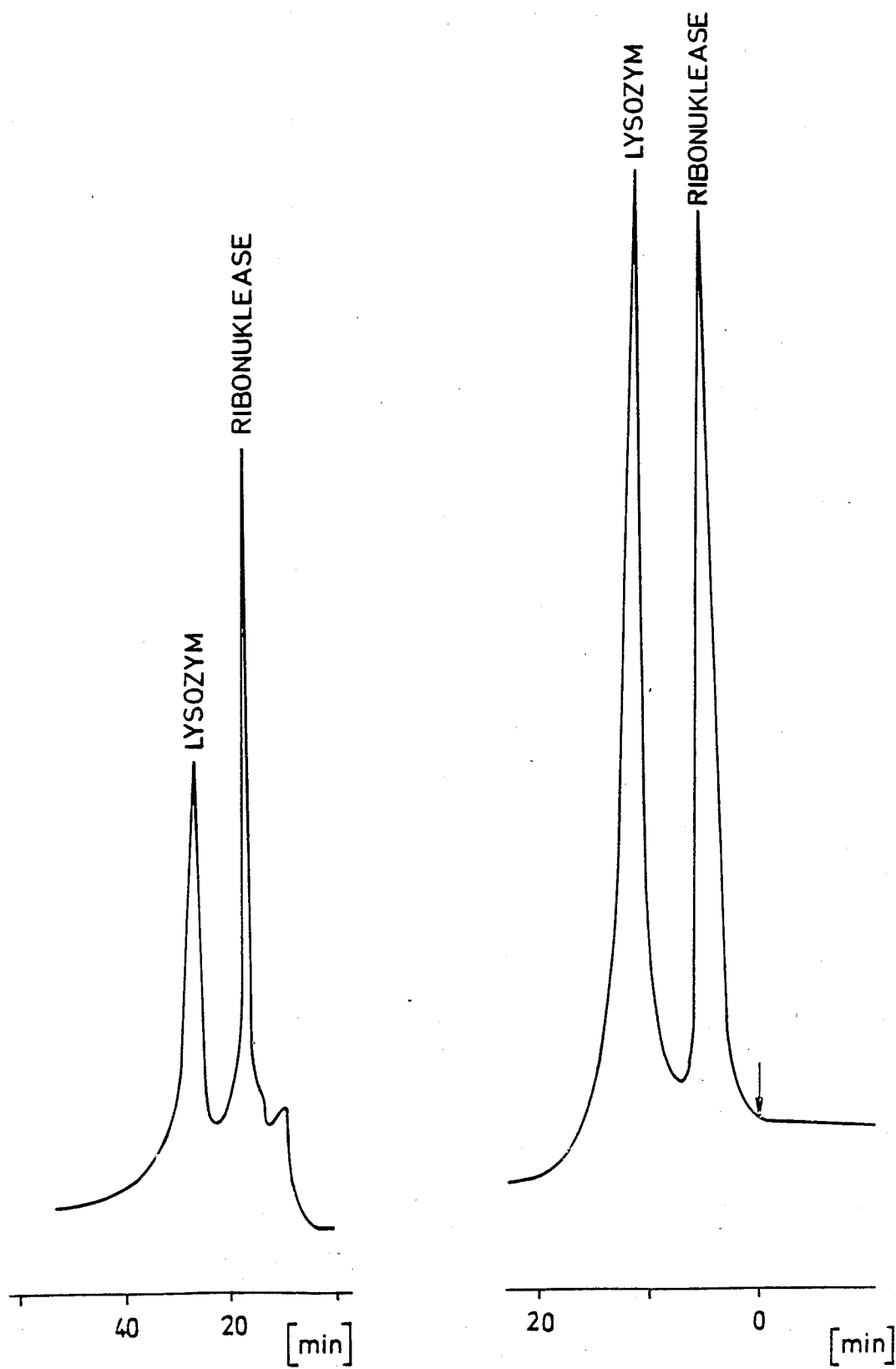

A mixture consisting of 0.1 mg ribonuclease and 0.1 mg lysozyme dissolved in 0.02 mol/l phosphate buffer with pH 6.8 was separated under the conditions identical with example 35 and in the same equipment, but with a membrane made according to example 31. The elution was carried out at flow rate 1 ml/min and pressure 0.1 MPa using the gradient of ionic strength in the same buffer, where increased the content of sodium chloride so that it reached 0.5 mol/l after 15 minutes. The result is shown in FIG. 3.

EXAMPLE 39

The same mixture of ribonuclease and lysozyme as in example 38 was separated under the identical conditions on a membrane prepared according to example 36. The chromatogram is shown in FIG. 4.

EXAMPLE 40

A mixture containing 150 mg ribonuclease, 100 mg ovalbumin, and 150 mg chymotrypsinogen was separated in an equipment having the shape of a prism and comprising a chamber with volume 10 ml with a wall formed by a rectangle membrane with area 6×8 cm and thickness 1.5 mm prepared according to example 11 and 19. The flow rate of eluent was 5 ml/min at pressure 0.8 MPa. The elution was carried out using the same gradient of ionic strength as in example 38 and the eluent was collected in test tubes in 10 ml portions. The fifth, sixth and seventh test tube contained 5, 85 and 10% ribonuclease, respectively, the eighth, ninth and tenth test tube contained 15, 75 and 10% ovalbumin, respectively, and, eventually, the twelfth, thirteenth, fourteenth, fifteenth and sixteenth test tube contained 3, 28, 16, 32 and 20% chymotrypsinogen, respectively.

EXAMPLE 41

Figure 5:
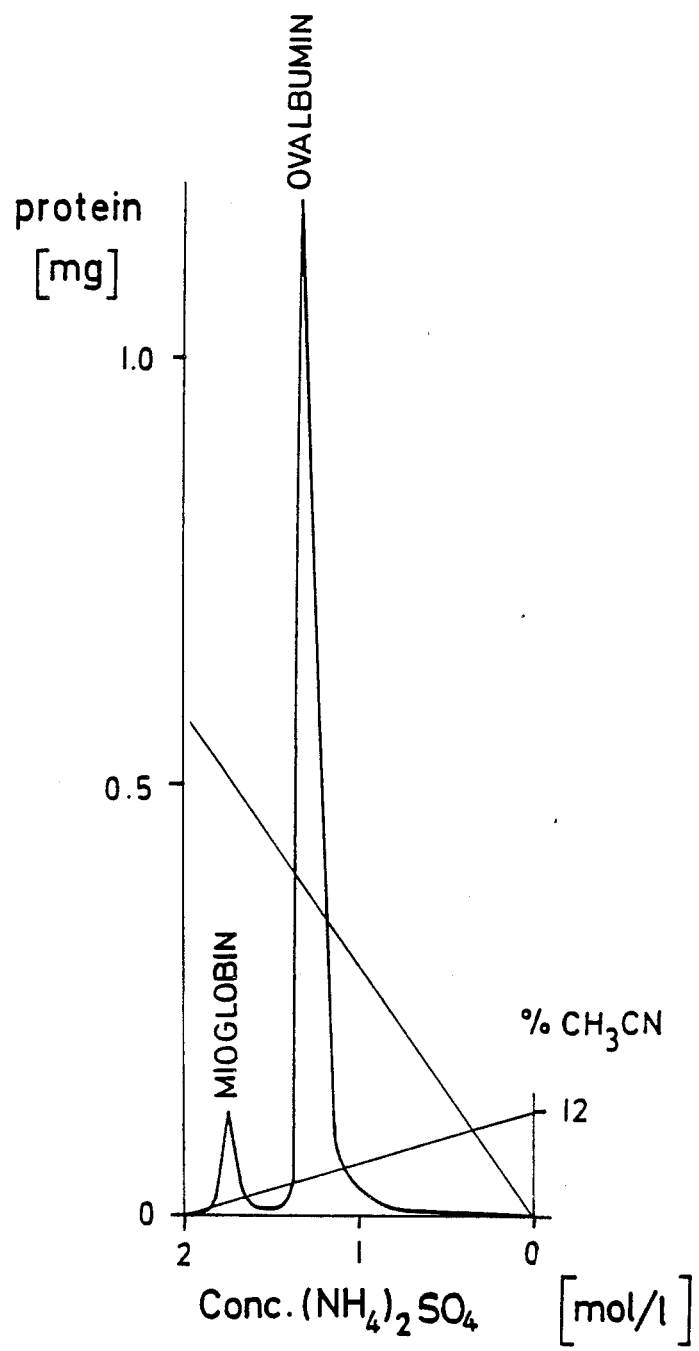

A mixture of 0.15 mg myoglobin and 0.3 mg ovalbumin was separated on the membrane and in the equipment according to example 35, with the distinction that acetonitrile was added into the buffer with decreasing ionic strength in such amount, that its concentration was 12 vol.% after 20 minutes at pressure 0.25 MPa. The separation is shown in FIG. 5.

We claim:

1. A method comprising: providing a macroporous membrane which comprises a copolymer of a monovinyl monomer, selected from the group consisting of acrylates, methacrylates, vinylpyridine, N-vinylpyrrolidone, vinyl acetate, and hydroxystyrene, and a dinvinyl monomer selected from the group consisting of alkylene and hydroxyalkylene diacrylates and dimethacrylates, divinylbenzene, and divinylpyridine, wherein the weight ratio of the respective types of monomers ranges from 5:95 to 95:5, formed of polymeric globules having a size from about 0.05 micron to about 0.5 micron, said globules being interconnected by covalent bonds to form communicating voids or pores between the globules, placing a section of said membrane having an arbitrary size and shape on a base to secure the membrane in a fixed position and to enable liquid to pass through the membrane, the base in combination with the membrane forming a chamber, filling the chamber with a solution of a polymer or mixture to pass through the membrane under a pressure of up to 1 MPa, allowing the polymer to be sorbed in the membrane, then introducing a solvent having predetermined properties into a region in front of the membrane, and eluting, detecting or collecting individual components of the separated mixture by varying pH, ionic strength, temperature, or concentration of the organic solvent, which is miscible with water, according to a predetermined protocol.

* * * * *

UNITED STATES PATENT AND TRADEMARK OFFICE
CERTIFICATE OF CORRECTION

PATENT NO.  : 4,923,610
DATED       : May 8, 1990
INVENTOR(S) : Frantisek Svec, Miroslav Bleha, Tatiana Borisovna Tennikova, Boris G. Belenkii It is certified that error appears in the above-identified patent and that said Letters Patent is hereby corrected as shown below:

On the first page, after "Inventors:" the inventorship designation should read as follows:

Frantisek Svec, Hrebec, Czechoslovakia; Miroslav Bleha, Praha, Czechoslovakia; Tatiana Borisovna Tennikova, Leningrad, Soviet Union; Boris G. Belenkii, Leningrad, Soviet Union.

Signed and Sealed this

Tenth Day of December, 1991

Attest:

HARRY F. MANBECK, JR.

*Attesting Officer*            *Commissioner of Patents and Trademarks*